United States Patent [19]
Rand et al.

[11] Patent Number: 5,137,516
[45] Date of Patent: Aug. 11, 1992

[54] TRIGGERED APPLICATION DEVICE FOR MEDICAMENT TO BE MORE DESCRIPTIVE OF THE INVENTION

[75] Inventors: Paul K. Rand; Philip M. Regan, both of Ware, United Kingdom

[73] Assignee: Glaxo Group Limited, London, England

[21] Appl. No.: 618,746

[22] Filed: Nov. 27, 1990

[30] Foreign Application Priority Data
Nov. 28, 1989 [GB] United Kingdom ............... 8926825

[51] Int. Cl.[5] ............................................. A61M 5/20
[52] U.S. Cl. ..................................... 604/136; 604/137
[58] Field of Search ............... 604/130, 134, 137, 136

[56] References Cited

U.S. PATENT DOCUMENTS

| | | | |
|---|---|---|---|
| 2,752,918 | 7/1956 | Uytenbogaart | 604/136 |
| 3,403,680 | 10/1968 | Sinclair et al. | |
| 3,556,100 | 1/1971 | Hurschman | |
| 3,605,742 | 9/1971 | Tibbs | |
| 3,712,301 | 1/1973 | Sarnoff et al. | 128/218 F |
| 3,882,863 | 5/1975 | Sarnoff et al. | 128/218 F |
| 4,226,235 | 10/1980 | Sarnoff et al. | 128/218 F |
| 4,329,988 | 5/1982 | Sarnoff et al. | 128/218 F |
| 4,403,989 | 9/1983 | Christensen et al. | 604/137 |
| 4,517,978 | 5/1985 | Levin et al. | 604/136 |
| 4,530,695 | 7/1985 | Phillips et al. | 604/134 |
| 4,578,064 | 3/1986 | Sarnoff et al. | 604/137 |
| 4,689,042 | 8/1987 | Sarnoff et al. | 604/136 |
| 4,787,891 | 11/1988 | Levin et al. | 604/136 |
| 4,902,229 | 2/1990 | Schmidtz et al. | 604/137 |
| 5,026,349 | 6/1991 | Schmitz et al. | 604/130 |

FOREIGN PATENT DOCUMENTS

| | | |
|---|---|---|
| WO85/02776 | 7/1985 | European Pat. Off. |
| 0338806 | 10/1989 | European Pat. Off. |
| 0262585 | 12/1988 | Fed. Rep. of Germany |
| 3900926 | 8/1989 | Fed. Rep. of Germany |
| 2015331 | 4/1970 | France |
| WO88/08725 | 11/1988 | PCT Int'l Appl. |
| 1206340 | 9/1970 | United Kingdom |

Primary Examiner—Paul J. Hirsch
Attorney, Agent, or Firm—Darby & Darby

[57] ABSTRACT

The application describes an administering device, in particular a self-injecting device, comprising a body for holding a container of a substance to be administered, a release mechanism, and means controlled by the release mechanism to discharge the said substance. The body is formed of two parts, one part being movable relative to the other, wherein one part has a trigger and the said release mechanism is partly actuated by the operation of a trigger of the said one part and partly actuated by movement of the other part relative to the said one part, but is only wholly actuated by both the operation of the trigger and the movement of the other part. Thus the discharge means cannot be accidentally actuated.

17 Claims, 10 Drawing Sheets

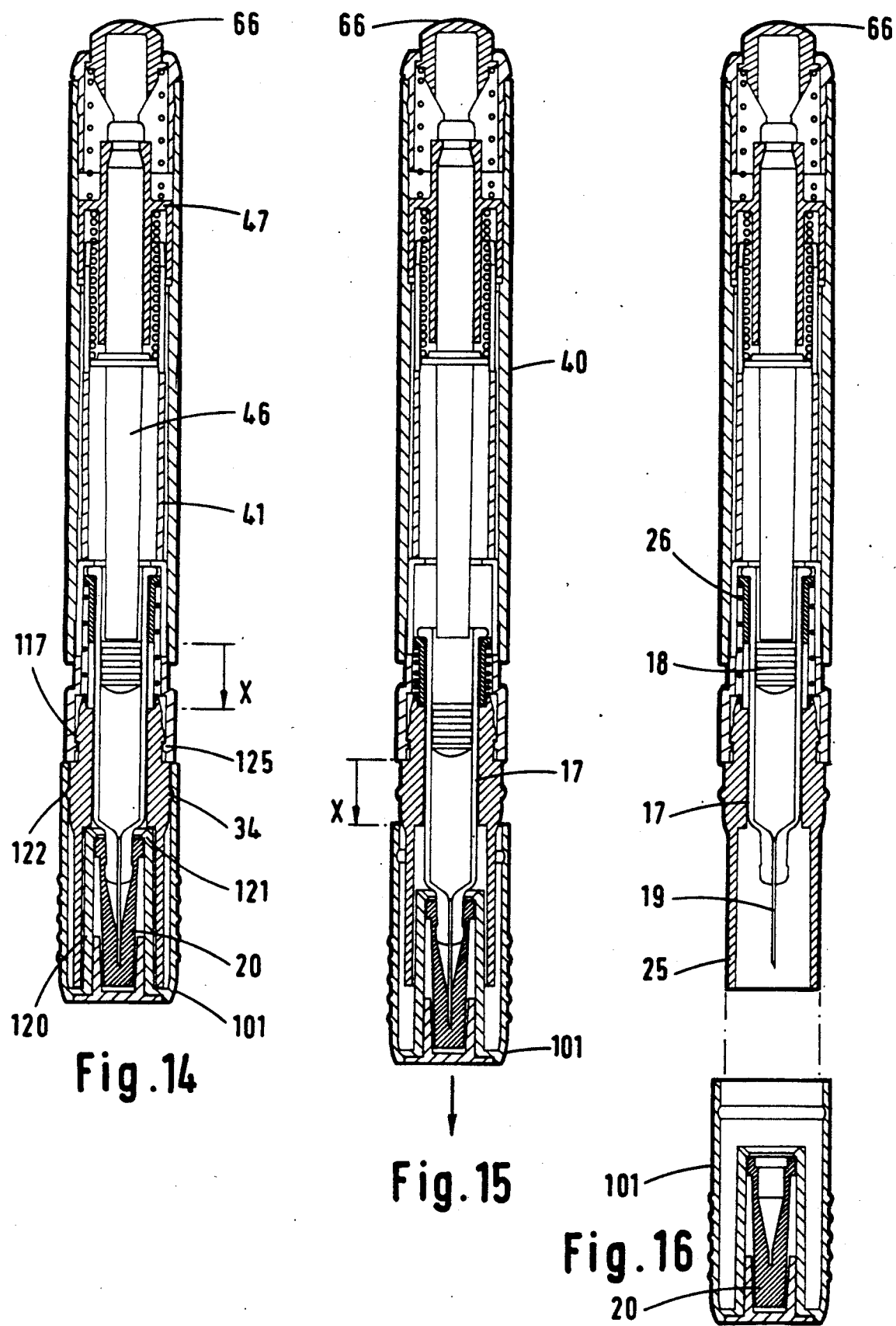

TRIGGERED APPLICATION DEVICE FOR MEDICAMENT TO BE MORE DESCRIPTIVE OF THE INVENTION

BACKGROUND OF THE INVENTION

The present invention relates to an administering device and in particular to an automatic self-injecting device for administering a predetermined dose of a pharmaceutical substance.

Self-injecting devices for delivering pharmaceutical compounds are known, in particular for use by diabetics to inject insulin. Such known devices tend to be complicated to load, unwieldy and noisy to use, and require very precise handling. However, since diabetics need to self-inject on a very regular basis, they learn to use the devices in time and become used to the disadvantages.

In one such known device, a pre-filled conventional syringe is loaded into a cylindrical delivery chamber and a piston is retracted against the force of a spring and then locked in position. To administer the insulin the device is placed against the skin, the spring is released by the depression of a button and the syringe is pushed by the piston into the skin, which piston then compresses the plunger of the syringe to inject the insulin. The syringe is thrown away after use and an unused syringe is loaded when a further injection is required. Devices such as that described above are shown in EP 0338806 (Owen Mumford Ltd), W088/08725 (Haselmeier), DE 3960926 (Dietronic) and DD 262585 (Tech Hoch, Merseburg), for example.

In another version of self-injecting device manufactured by Owen Mumford Ltd (not described in any patent literature known to the applicants) the release button is on the side of the device and is locked in position by a catch to prevent accidental actuation. The catch can be disengaged from the button by a sliding movement along the length of the device.

U.S. Pat. Nos. 4329988, 4226235, 3882863 and 3712301 (all in name of Survival Technology Inc.) concern devices for administering antidotes to be used by military personnel in the event of chemical warfare These automatic injectors are actuated by being pressed against the user's thigh. Premature actuation is prevented by means of a safety cap which has a central pin which prevents the piston being released

BRIEF SUMMARY OF THE INVENTION

There remains a need in the art for an improved self-injecting device which is safe and easy to use and preferably is unobtrusive. The device should be usable by even the most inexperienced person one-handedly and should be able to deliver a small, precise dose by either subcutaneous or intramuscular routes. The present invention is therefore intended for use by naive users, unaccustomed to the use of self-injecting techniques, though of course it will also be advantageous, for regular users.

The above-mentioned need arises because there are some pharmaceutical compounds, for example sumatriptan which is useful in the treatment of migraine and related disorders such as cluster headache, which are only administered in small doses and relatively infrequently and so the user does not become practised at using the injecting device Further, because migraine attacks can come on suddenly, there is a need for a device which is compact, is portable and can be used quickly and discretely.

According to the present invention there is provided an administering device comprising a body for holding a container of substance to be administered, a release mechanism, and means controlled by the release mechanism to discharge the said substance, wherein the body is formed of two parts, one part being movable relative to the other, wherein one part has a trigger and wherein the said release mechanism is partly actuated by the operation of the trigger of the said one part and partly actuated by movement of the other part towards the said one part, but is only wholly actuated by both the operation of the trigger and the movement of the other part, whereby the discharge means cannot be accidentally actuated.

Preferably, one part of the body is slidably mounted within the other and extends out of the other. In a preferred embodiment, the release mechanism is mounted at an end of the one of the two parts which is mounted within the other part, the trigger of the other part being in the form of a pushbutton towards which the release mechanism is moved by movement of the one part within the other.

Preferably the container is a syringe held within the above mentioned one part. Actuation of the discharge means firstly moves the syringe forward within that one part to expose the needle, and thus to urge it through the skin, and secondly depresses the plunger of the syringe to administer the substance to the user. The syringe may be held within the one part against the action of a spring.

In a preferred embodiment, the administering device is elongate, slim and generally cylindrical and thus may be similar to a pen in shape. The discharge means within the device may be an elongate pusher rod which is urged by means of a resilient force.

The release mechanism may comprise a pair of arms over which the end of the pusher rod is held, the rod being released by relative movement of the button to separate the arms.

The one part of the device which moves within the other is preferably itself comprised of two parts, a first part extending out of the device and being in the form of a sleeve for holding the syringe, and a second part within the device which houses the pusher rod, the first and second parts of the one part being releasably connectable together.

The sleeve for the syringe may itself be formed of two parts, an inner and an outer sleeve movable relative to one another against the action of a spring.

In all embodiments of the invention, the great advantage is that the administering device cannot be accidentally set off. Thus, the release mechanism can only be actuated by two quite distinct movements, the operation of the trigger and the movement of one part of the device relative to the other. The trigger is in the preferred embodiments at the remote end of the device so that the two operations cannot occur together except by very deliberate action.

In one aspect of the invention, the administering device is provided together with a housing for at least one container of the substance to be discharged, the housing comprising a removable sleeve for the container, means releasably holding the sleeve within the housing, and a container within the sleeve, the said sleeve having means to releasably attach itself to the administering device, whereby the sleeve and container can be removed from the housing by co-operation with the administering device and can be returned to the housing after use.

Preferably, the housing has a lid which is closed after the used container is returned thereto. The container is preferably a syringe and the syringe may have a rubber cap protecting the needle, this cap remaining within the housing when the sleeve is removed by the administering device.

Preferably, the syringe is held within the sleeve against the action of a spring. The releasable attaching means of the sleeve may in one embodiment be at a screw fitting, though could alternatively be a bayonet groove and tongue fitting or a snap-fit.

Most preferably, the housing and the administering device are provided within a single casing. The casing may have a recess for the administering device, this recess including means to prime the release mechanism when the device is placed into the recess.

The advantage of this arrangement is that individual containers of the substance to be administered can be safely stored before use, without any danger to the user being injured by the exposed needle. In the first place, each syringe is housed within the sleeve and in the second case, the needle of each syringe is covered by a rubber cap. The syringes are easily loaded onto the administering device without the user having to make any direct contact with the syringe and the used syringes are returned to the housing and retained therein, again without the user having to directly touch the syringe.

The housing is preferably provided as a disposable unit which is safely disposed of after the or each syringe has been used.

In another embodiment of the invention, the container is moveable within the body against the discharge means and the device further comprises means to prevent discharge of the substance until the discharge means is engaged by the release mechanism, whereby the loading of the container into the body can simultaneously engage the discharge means with the release mechanism.

Where the container is a syringe, a rubber cap can be provided over the syringe needle to seal the syringe, so that the syringe itself can be used to move the discharge means, typically against the action of a spring.

In all embodiments, the syringe may advantageously contain a pharmaceutical substance, for example sumatriptan, of use in the treatment of migraine and related disorders such as cluster headache.

Preferred embodiments of the invention are described in more detail below, by example only, with reference to the accompanying drawings.

BRIEF DESCRIPTION OF THE DRAWINGS

FIG. 6 is a sectional view showing the fitting of the administering device within the housing to connect the sleeve to the administering device.

DETAILED DESCRIPTION

Figure 1:
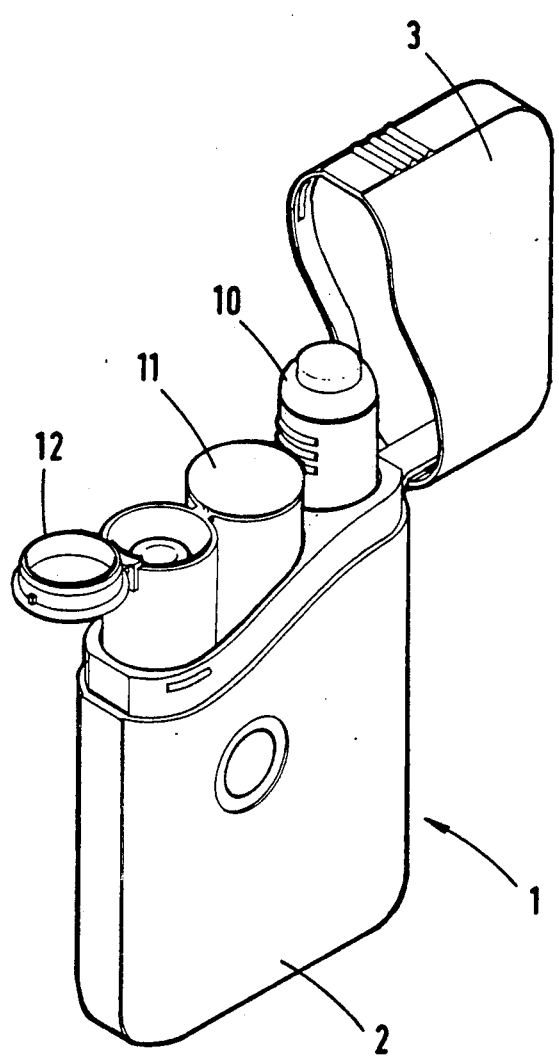
FIG. 1 is a perspective view of a casing holding an administering device and a housing according to one aspect of the invention.
Figure 2:
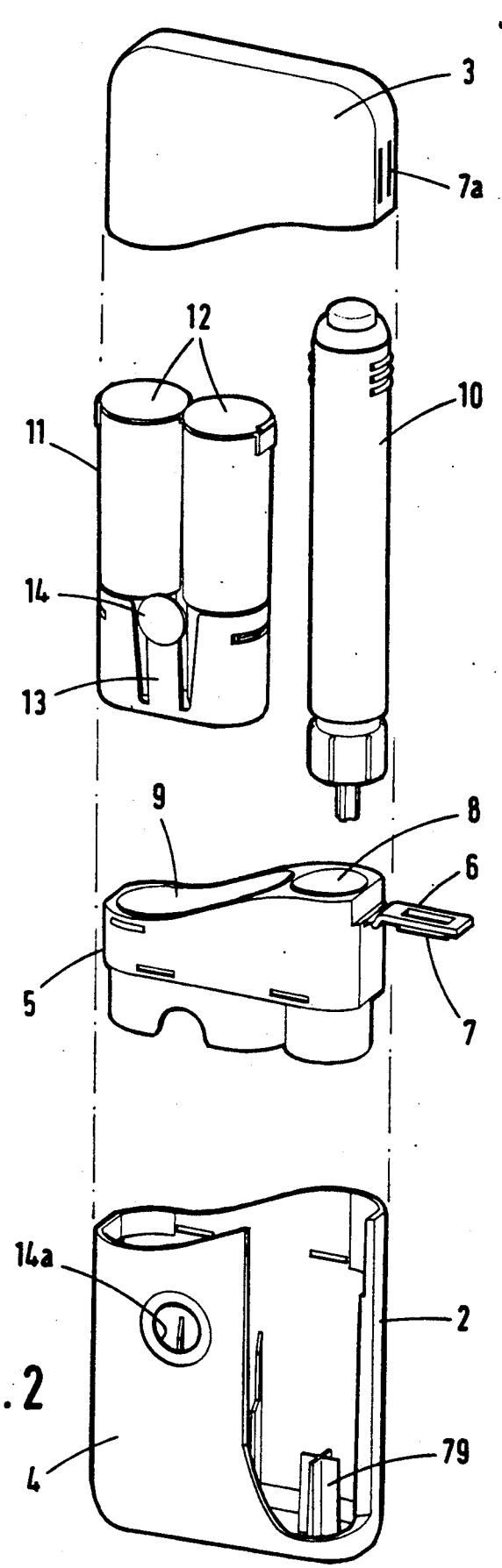
FIG. 2 is an exploded view showing the casing, administering device and housing of FIG. 1.

FIG. 1 shows in perspective view the syringe casing 1 consisting of a body part 2 and cap 3 which is hinged to the body part 2. When the cap 3 is closed, the casing 1 is pleasing to the eye and fits neatly in the user's pocket or handbag. As more clearly shown in the exploded view of FIG. 2, the body part 2 of the casing comprises a molding 4 into which is snap fitted a casing insert 5 having an integral hinge 6 including two snap-fit lugs 7 for location in corresponding holes 7a in the cap. The casing insert 5 comprises a cylindrical recess 8 and a generally oblong recess 9 adjacent the cylindrical recess.

The recess 8 is for syringe administering device 10 and the oblong recess 9 is for a syringe cartridge housing 11. In the illustrated embodiment, the syringe cartridge housing 11 contains two disposable syringe cartridges, but in other embodiments it may have only one syringe cartridge or more than two cartridges.

The casing insert 5 snap-fits into the molding 4 and the syringe cartridge housing 11 snap-fits into the casing insert 5 and into the molding 4 with reclosable caps 12 uppermost. Flexible arms 13 on the cartridge housing 11 each have a circular pad 14 at their ends, this pad fitting into corresponding circular holes 14a on either side of the molding 4. In use, the pads 14 are pressed in order to remove the housing 11 when it needs replacement.

Figure 3:
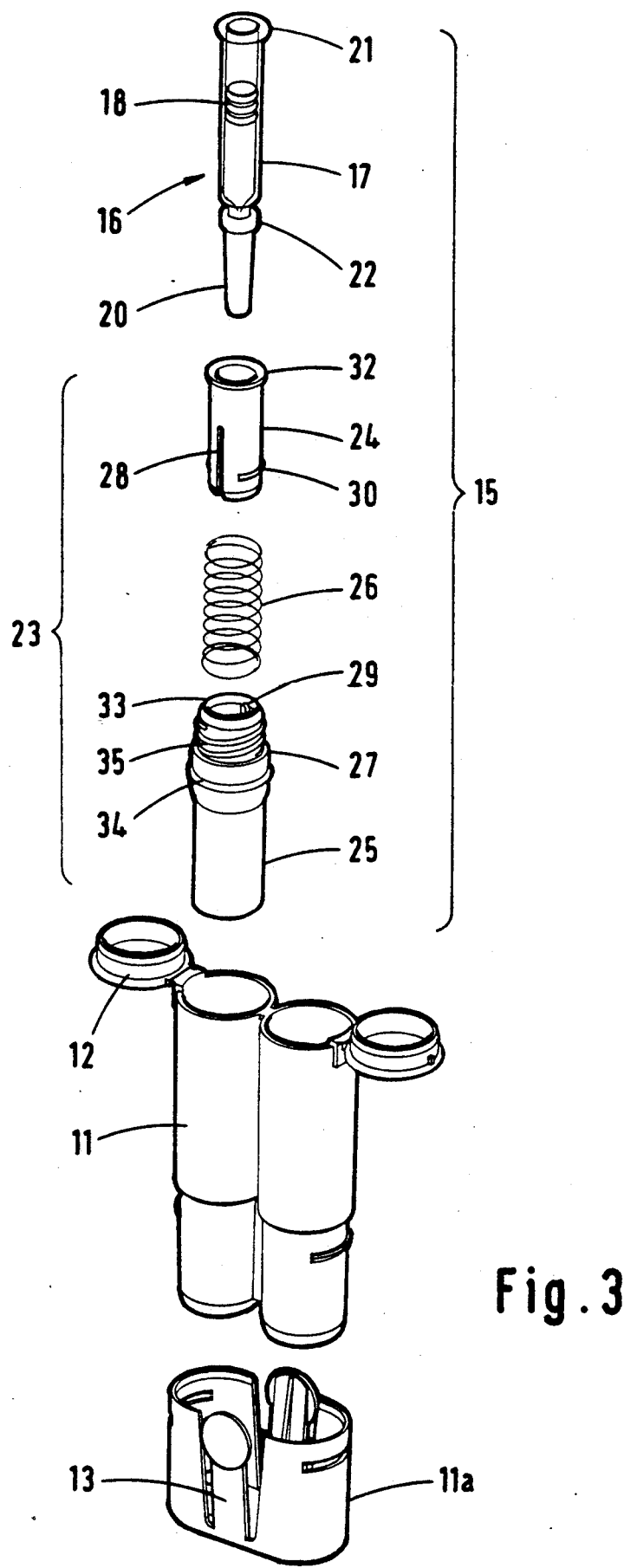
FIG. 3 is a perspective exploded view of the housing of FIGS. 1 and 2.

The syringe cartridge housing 11 is shown in more detail in FIG. 3. In this figure one syringe cartridge 15 is shown in exploded view. The housing 11 includes a housing base part 11a which snap-fits into the housing, the base part having the flexible arms 13 mentioned above.

Each syringe 16 which is contained in the twin syringe cartridge housing 11 is prefilled with a predetermined amount of a drug and comprises a glass barrel 17 containing the drug and stopped by a rubber stopper 18. The syringe needle 19 (not shown in this figure) is protected by a rubber septum 20. The barrel has a lip 21 and the septum has a rim 22. The syringe is located within a sleeve assembly 23 consisting of an inner sleeve 24 and an outer sleeve 25 with a light spring 26 there between. The fitting of the syringe will be described in more detail later. The sleeve assembly 23 is push fitted within the syringe cartridge housing 11, as described later on.

Figure 4:
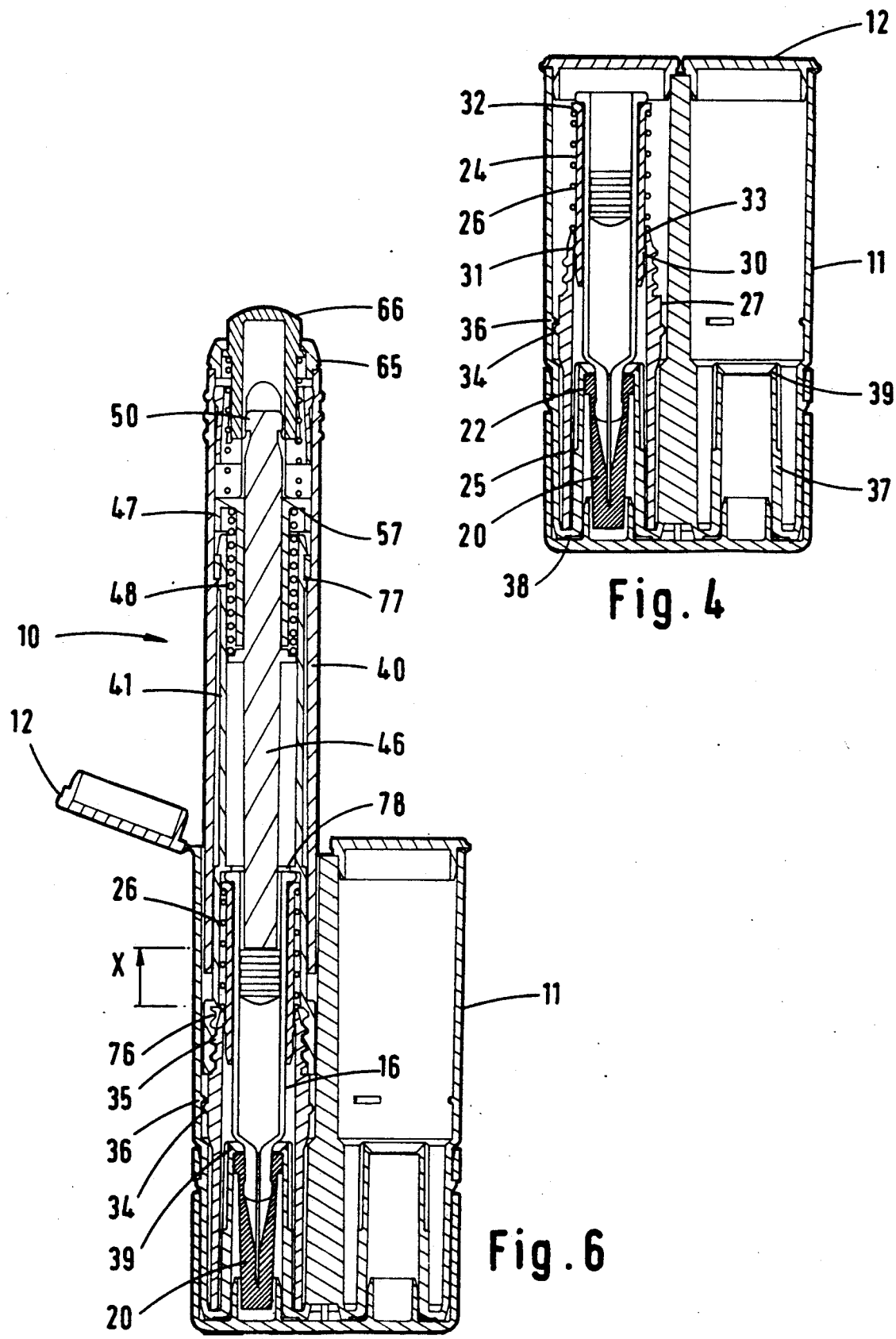
FIG. 4 is a sectional view of the housing of FIG. 3.

As can also be seen in FIG. 4, the inner sleeve 24 fits within the upper portion 27 of the outer syringe sleeve 25, this fitting being permitted by virtue of the slots 28 in the inner syringe sleeve 24 which allow the sides of the sleeve to be flexed inwardly. Slots 28 fit over longitudinal webs 29 on the inside of the outer sleeve 25. This fitting prevents rotation of the inner sleeve 24 relative to the outer sleeve 25. Also, the webs 29 limit the movement of the inner sleeve 24 into the outer sleeve 25, i.e. when the webs 29 are at the end of the slots 28 no further movement is possible. After the inner sleeve 24 has been located within the outer sleeve 25, external protrusions 30 on the inner sleeve locate beneath an internal annular lip 31 at the top of the outer sleeve 25. Thus, the inner sleeve cannot move out of the outer sleeve. Movement of the inner sleeve 24 into the outer sleeve 25 is against the action of the light spring 26 which locates between the upper rim 32 of the inner sleeve and the upper end 33 of the outer sleeve 25.

The outer syringe sleeve 25 comprises intermediate its ends an annular rim 34, and around its upper end has a screw thread 35 for connection to a correspondingly threaded part of the syringe actuating device. This connection will be described later.

The order in which the component parts described above are assembled is as follows. The light spring 26 is placed in a position around the inner syringe sleeve 24. The inner syringe sleeve 24 is located within the outer syringe sleeve 25. The sleeve assembly is then pushed within the syringe cartridge housing 11 until the rim 34 locates under a ridge 36 on the inside of the cartridge housing. The syringe 16 is then pushed within the sleeve assembly until the lip 21 at the upper end of the syringe barrel engages the end of the inner sleeve 24.

FIG. 4 shows the sleeve assembly fitted in the cartridge housing 11 and one syringe 16 fitted into the sleeve assembly 23. In this position, the lower end of the outer sleeve 25 surrounds a hollow cylindrical protrusion 37 at the base 38 of the housing. This protrusion is more clearly seen in the right hand recess of the cartridge housing 11. On the inside of the upper rim of the cylindrical protrusion 37 there is a lip 39. As the syringe 16 is pressed into the sleeve assembly within the housing 11, the rim 22 of the rubber septum 20 will engage under this lip 39.

Figure 5:
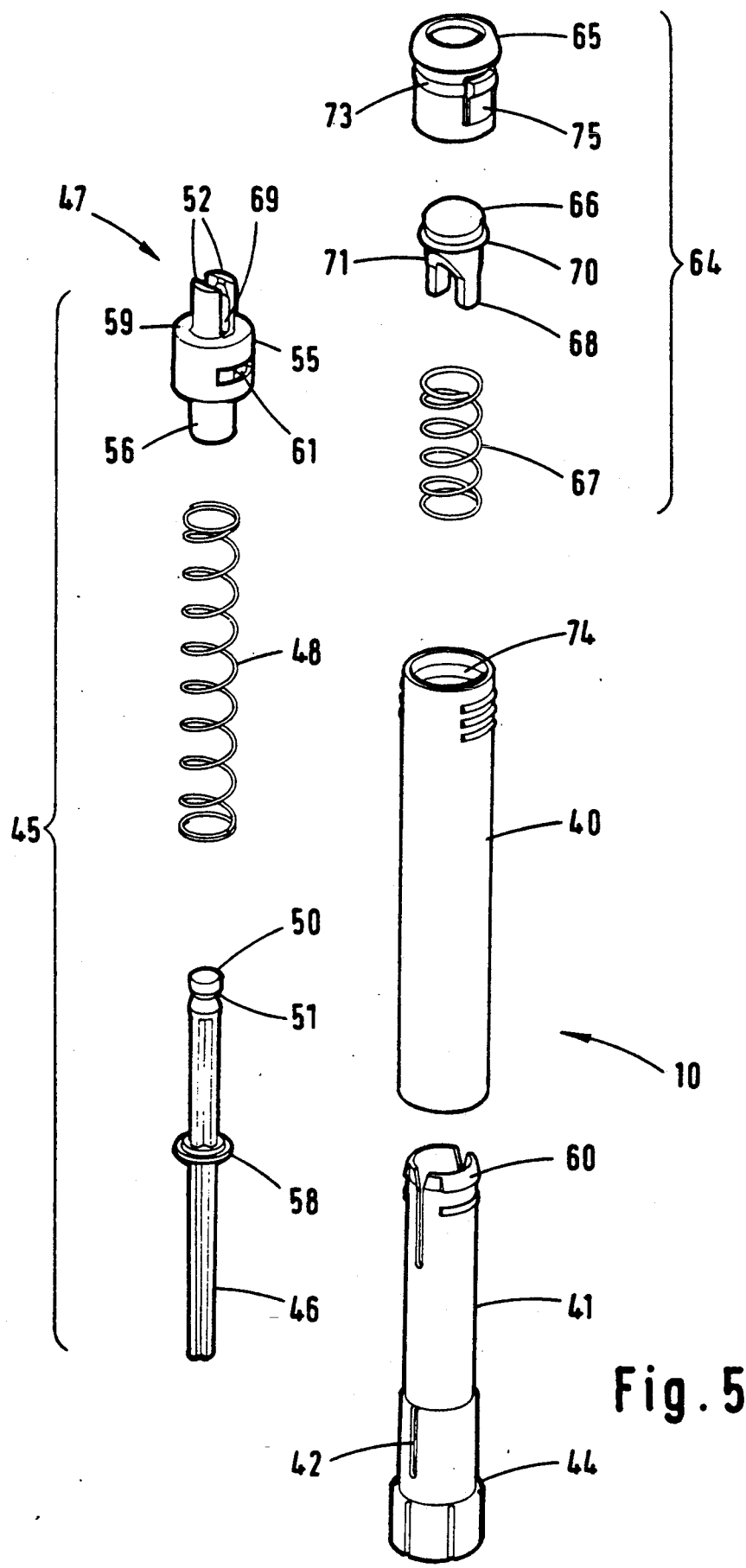
FIG. 5 is an exploded perspective view of the administering device of FIG. 1, without the sleeve which is in the figures still contained within the housing.

FIG. 5 shows an exploded view of the syringe actuating device 10. The actuating device 10 comprises an external casing 40 and an internal shaft 41 which slides within the external casing 40. Slots 42 on the internal shaft 41 and slide over longitudinal internal webs 43 (not seen) of the external casing 40 and prevent rotation of the internal shaft 41 relative to the casing 40. The lower part of the internal shaft 41 has a larger diameter and a shoulder 44 is formed between this wider part and the remainder of the shaft.

Within the internal shaft 41 is mounted a plunger assembly 45 comprising a pusher rod 46 and a retention clip 47, urged apart by a spring 48. At the top of the pusher rod is a head 50 which is separated from the rest of the pusher rod by a narrower neck portion 51. The head portion 50 clips over the top of two arms 52 of the retention clip 47.

The retention clip 47 also comprises a main hollow body portion 55 and a narrower cylindrical protrusion 56 extending out of the body portion 55 and for location in the end of the internal shaft 41. The internal shoulder 57 (see FIG. 6) between the body portion 55 and the narrower portion 56 defines a seat for the spring 48. The seat for the other end of the spring 48 is defined by an annular rim 58 on the pusher rod 46. Shoulder 59 is formed between the arms 52 and the body portion 55.

Lips 60 at the upper end of the internal shaft 41 clip within circumferential slots 61 in the body portion 55 of the retention clip 47.

The actuating device also comprises a resilient trigger device 64 comprising a cap 65 defining a seat for an actuating button 66, together with a button spring 67. The actuating button 66 comprises a pair of arms 68 which locate within the slots 69 between the arms 52 of the retention clip 47. The spring 67 is held between an annular rim 70 on the actuating button 66 and the shoulder 59 of the main body of the retention clip. At the end of the two arms 68 nearest to the rim 70 of the actuating button, there is an inclined portion 71; in other words, each arm 68 flares as it approaches the button portion.

This flared portion of each arm when pushed into the slots 69 will tend to separate the arms 52 of the retention clip 47.

The cap 65 for the button 66 clips inside the casing 40, an annular protrusion 73 on the outside of the cap 65 fitting in an annular recess 74 on the inside of the external casing 40. The cap 65 also has a pair of flexible arms 75 which partly define the protrusion 73 and which, when the cap is fitted in the external casing 40, are forced inwardly to restrict the travel of the button 66. It should also be noted that on the inner surface of the bottom of the internal shaft 41 is a screw thread 76 (see FIG. 6) for connection to the screw thread 35 of the outer cartridge sleeve 25. The fitting together of the components of the actuating device will be described in further detail with reference to FIG. 6.

The assembled actuating device 10 can be seen, in sectional view, in FIG. 6, which also shows the actuating device 10 located in the cartridge housing 11. In use, the cartridge housing is of course in the casing 1 of FIGS. 1 and 2.

As seen in this figure, the internal shaft 41 is inserted into the external shaft 40 from below, the pusher rod 46 and the spring 48 are inserted into the internal shaft from above, the retention clip 47 is pushed onto the end of the internal shaft 41 and the cap 65 clips inside the end of the external casing 40.

It should be noted that internal shoulder 77, against which the main body 55 of the retention clip 47 abuts, prevents the internal casing 41 from coming out of the external casing 40 and that an internal rim 78 prevents the pusher rod 46 from coming out of the internal shaft 41.

To force the pusher rod 46 into the position where its head 50 is over the arms 52 of the retention clip 47 demands that the pusher rod 46 is moved against the action of the spring 48. This can either be done by using a suitable device to push the rod 46 within the external casing 40, but most preferably it is achieved by pressing the actuating device 10 within the cylindrical recess 8 of the main casing 1. The main casing 1 has at its base an elongate protrusion 79 (see FIG. 2) aligned with the recess 8 which, when the actuating device 10 is pressed into the recess, will force the pusher rod 46 upwardly to engage the head of the pusher rod over the arms 52 of the retention clip 47. In fact, the casing 1 cannot be closed unless pusher rod is engaged in this way. Thus, the spring 48 of the actuating device 10 can be cocked in a simple and unobtrusive manner and the device is always ready for use.

The actuating device 10 is located within the cartridge housing 11 by simply sliding it in so that the internal shaft 41 surrounds the inner cartridge sleeve 24. When the actuating device has been pushed fully in, it is rotated to engage the screw thread 76 of the internal shaft 41 with the screw thread 35 of the outer cartridge sleeve 25.

To remove the syringe cartridge from the cartridge housing 11 the actuating device 10 is simply pulled out from the housing. The initial pull on the actuating device releases the sleeve assembly 23 from the housing 11 by disengaging the ridge 36 and rim 34. After this movement, the syringe 16 however remains in the same position with respect to the housing 11 because the force required to remove the rubber septum 20 from the syringe 16 is greater than the force of the spring 26 of the syringe.

Further upward movement of the actuating device 10 compresses the syringe spring 26 until the webs 29 of the outer sleeve 25 are at the end of the slots 28 of the inner sleeve 24. Further upward movement therefore releases the syringe 16 from the cartridge housing 11, though the rubber septum 20 remains within the housing 11, held by the lip 39 of the cylindrical protrusion 37 at the base of the housing 11. The upward movement of the actuating device 10 before the syringe is released is shown by dimension X in FIG. 6. As the complete syringe actuating device 10 is removed from the housing 11, the syringe spring 26 expands to move the syringe upwardly within the sleeve assembly 23 back to its original position.

Figure 8:
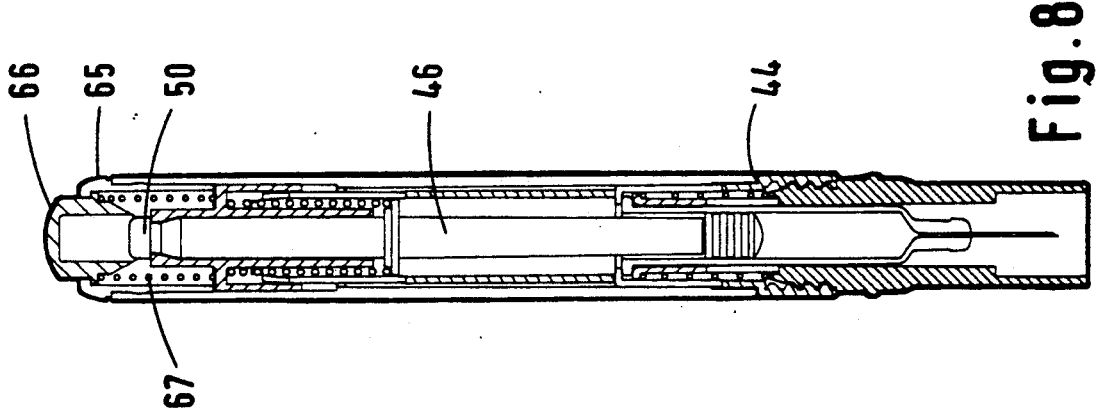
Figure 7:
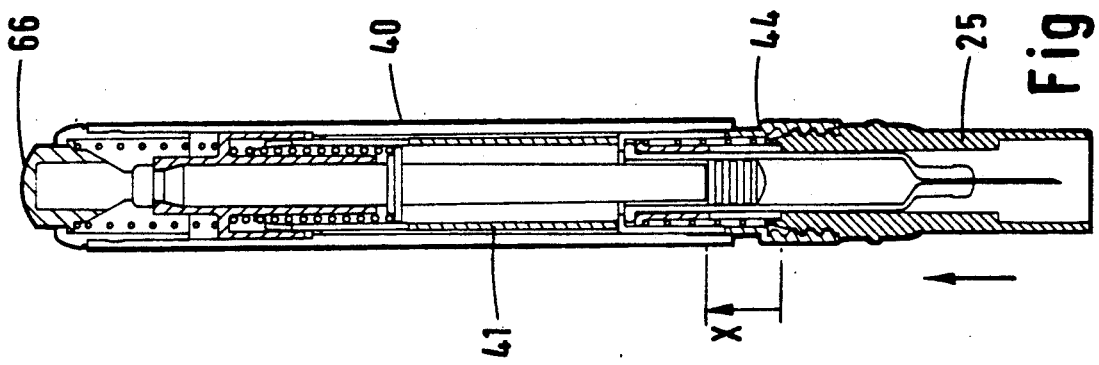

The self injecting syringe device is now ready for actuation by the user. The actuation steps are illustrated in FIGS. 7 to 10. As illustrated in FIGS. 7 and 8, the first step is the movement of the internal shaft 41 and sleeve assembly 23 (which contains the syringe), within the external casing 40. This movement is achieved by the user pressing the device 10 against the area of injection. In the following, the user's thigh is referred to, but this is only an example. The relative movement is limited by the shoulder 44 of the internal shaft 41 abutting against the bottom of the external casing 40. This movement compresses the button spring 67 and moves the retention clip 47 upwardly toward the actuating button 66. During the movement, the arms 68 of the actuating button 66 move within the slots 69 of the retention clip 47. At the end of this movement, the flared parts 71 of the arms 68 of the button are adjacent the ends of the slots 69 of the retention clip.

Depression of the actuating button forces the flared portions 71 of the button arms 68 into the slots 69 of the retention clip, thereby separating the arms 52 of the retention clip. It should be noted that depression of the button 66, without the movement of the internal shaft 41, would not be sufficient to move the flared portions 71 into the slots 69, the downward travel of the button 66 being restricted by the arms 75 of the clip 65.

Figure 9:
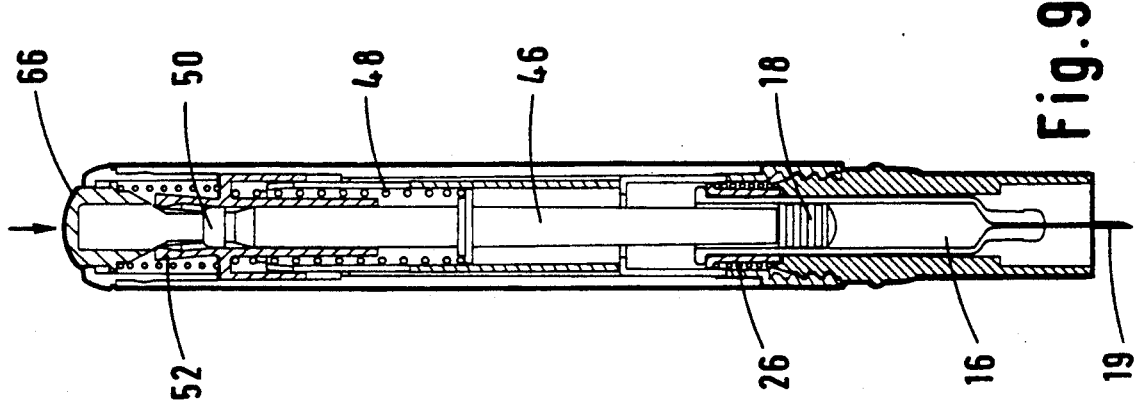

As seen in FIG. 9, the separation of the arms 52 releases the head 50 of the pusher rod 46 and the pusher rod is therefore moved forwardly by the force of the main spring 48. The pusher rod 46, which engages the plunger 18 of the syringe 16, firstly moves the entire syringe 16 downwardly, against the force of the syringe spring 26. This movement, which exposes the needle 19, does not depress the plunger 18 of the syringe 16 because the force required to expel the fluid from the syringe is greater than the force of the spring 26. Therefore the movement of the pusher rod 46 does not yet force the fluid from the syringe. It should be noted that the downward movement of the syringe 16, that is the needle penetration depth, is determined by the slots 28 and webs 29 of the sleeve assembly 23.

Figure 10:
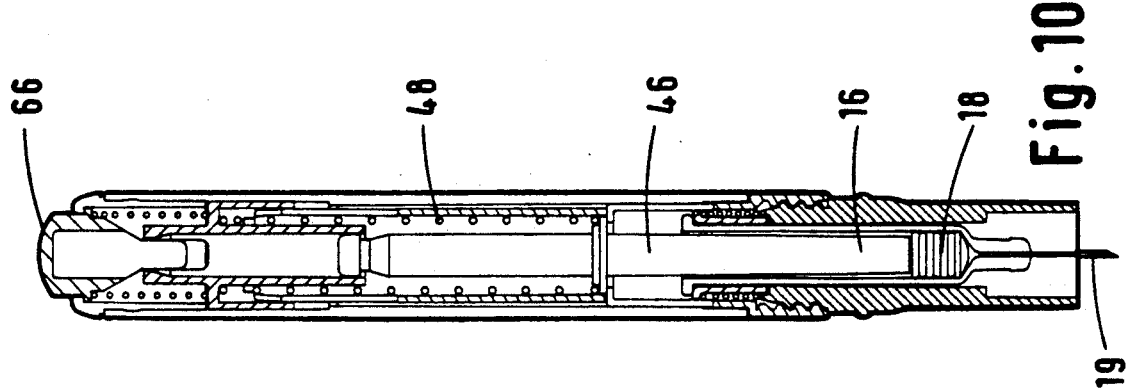
FIGS. 7 to 10 are sectional views of the complete administering device, including the sleeve, showing the operation of the device to administer the substance which is within the syringe, these views being perpendicular to the sectional view of FIG. 6.

The final stage, illustrated in FIG. 10, is the depression of the syringe plunger 18 by the pusher arm 46. Thus, after the needle 19 has been exposed and penetrates the skin of the user, the syringe 16 is emptied to administer the drug to the user.

It should be noted that the initial pressure of the device on the patient's thigh, which provides for the first movement, tensions the skin which means that when the needle penetrates the skin there is little chance of lateral movement of the needle relative to the skin, and therefore the injection is relatively painless.

Moreover, as mentioned above, since neither the depression of the button 66 nor the movement of the inner shaft 41 relative to the external casing 40 can by themselves release the pusher arm 46, the device is inherently safe and cannot be accidentally set off.

While it is preferred that the device first be pressed against the thigh, and then the button depressed, the device will of course be triggered if the button is depressed, and held down, and the device then pressed against the arm.

After the drug has been administered, the device 10 is removed from the user's thigh and the spent syringe cartridge is disposed of back within the syringe cartridge housing 11 from which it came. Thus, the device 10 is again pushed in the housing 11 so that the sleeve assembly 23 clips therein. The actuating device 10 is then twisted in a reverse direction to release the screw threads 35 and 76, and the device, without the sleeve assembly 23 and syringe 16, is removed. Pushing the syringe sleeve assembly into the housing in this way will of course move the syringe 16 upwardly within the sleeve 21 and the needle will be covered by the rubber septum 20. The cap 12 of the cartridge housing 11 is closed to seal the spent syringe in the housing. The spent cartridge cannot be accessed without using the actuating device. The used syringe is thus disposed of in a neat and entirely hygienic manner.

The actuating device 10 can be replaced within the cylindrical recess 8 for future use, and the casing 1 can be closed. The replacing of the actuating device within the recess 8 moves the pusher arm 46 upwardly and cocks the main spring 48 for the next use, as described above.

A second embodiment of the invention is illustrated in FIGS. 11 to 16. A principal difference between the administering device shown in these figures and that shown in the earlier figures is that this device is intended to be delivered to the user in a ready to use state. In other words, the user does not have to set the release mechanism or load the syringe assembly himself. Furthermore, it is intended that this ready to use device is completely disposable so that after the substance has been administered, and the syringe emptied, the entire assembly of actuating device and syringe cartridge is discarded. The user will have a number of complete administering devices for future use.

This administering device is, however, very similar to that described earlier and therefore where appropriate the same numerals are used. In particular, the syringe actuating device 10 is substantially identical and includes the external casing 40 with the internal shaft 41 moving therein. A pusher rod 46 is mounted within the internal shaft 41 against the action of a spring 48, the head 50 of the pusher rod being held by the retention slip 47. Furthermore, the arrangement of the syringe 16 in the sleeve assembly 23 is the same as in the first embodiment, with the exception of the connection to the actuating device 10, as described later.

As in the earlier embodiment, the administering device can only be actuated by both a depression of the button 66 and the relative movement of the internal shaft 41 and external casing 40. In other words, the operation of the device to administer the contents of the syringe described in relation to the first embodiment applies equally to the present device.

Figure 11:
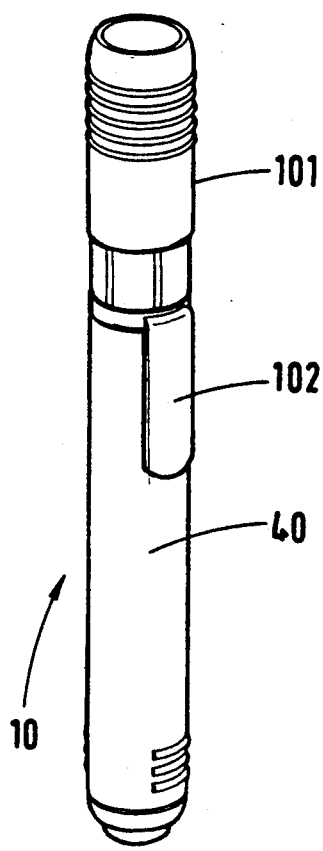
FIG. 11 is a perspective view of a complete administering device according to a second embodiment of the invention.

The complete administering device is shown in FIG. 11. In this figure is seen the external casing 40 and a pull-off cap 101, together with a pen ? lip 102 which fits around the body of the administering device 10. As is clearly seen in this figure, the entire device is—as in the first embodiment—of a similar size and shape to a pen and the pen clip 102 allows the device to be carried around in the user's pocket in the same way as if it were a pen.

Figure 12:
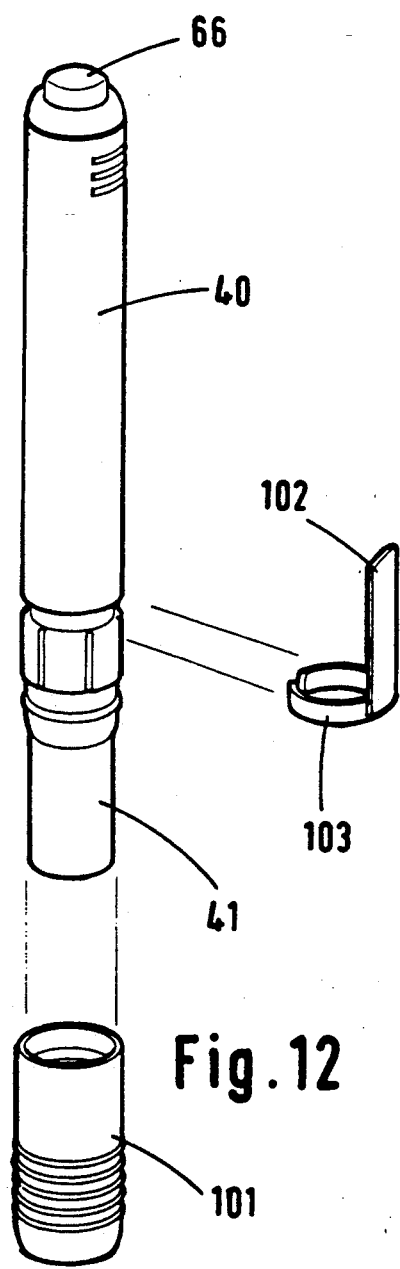
FIG. 12 is an exploded perspective view of FIG. 11.

The exploded view of FIG. 12 shows the administering device in a ready to use state. In this view, the device has been inverted and the actuating button 66 is visible. The pen clip 102 is removed from the device, this being possible by virtue of the flexible wings 103 of the pen clip. The removal of the pen clip 102 allows the internal shaft 41 to move relative to the external casing 40. Before the pen clip 102 is removed, such movement is prevented.

Also in this figure is seen the removal of the pull off cap 101. The removal of this cap and the complete preparation of the device for use is described in more detail later.

Figure 13:
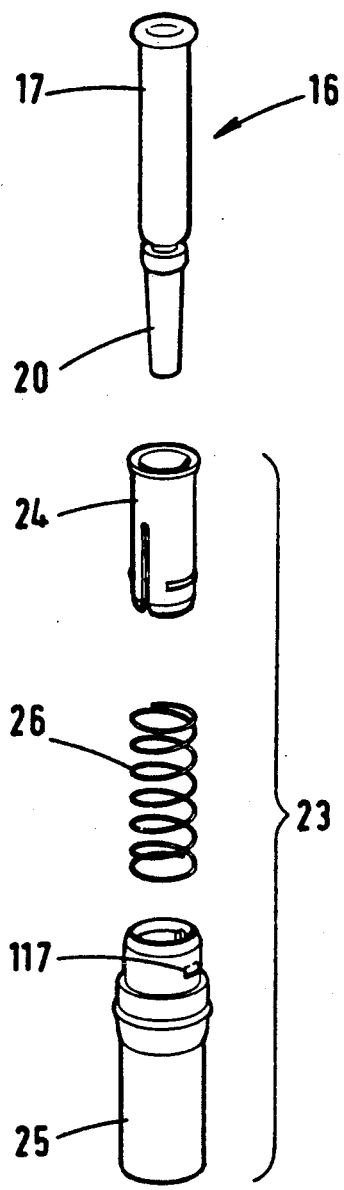
FIG. 13 is an exploded perspective view of part of the device of FIGS. 11 and 12, FIGS. 14 to 16 are sectional views of the device of FIGS. 11 and 12.

In FIG. 13 is shown, in an exploded view, the syringe assembly 23 and the pull off cap 101. The syringe 16 of this device is the same as that of the earlier embodiment and includes a glass barrel 17 and a rubber septum 20. The syringe 16 is located within an assembly of two syringe sleeves, an inner sleeve 24 and an outer sleeve 25, as in the previous embodiment, with a light spring 26 therebetween.

The difference between the sleeve assembly of FIG. 13 and that of FIG. 3 is that the outer sleeve 25 does not have a threaded upper portion. Instead lugs 117 on the outside of the upper portion of the outer sleeve 25 are provided. Corresponding lugs 125 (see FIG. 14) are provided on the inside of the internal shaft 41.

It can be seen in FIG. 13 that the pull off cap 101 includes a grip 118 area for ease of use and an end cap 119 which fits permanently in the cap 101.

The inside of the pull off cap 101 is seen in the sectional views of FIGS. 14 to 16. In a similar fashion to the cartridge housing 11 of the earlier embodiment, the pull off cap 101 includes an internal hollow cylindrical protrusion 120 with lip 121 for retaining the septum 20. In fact, the fitting of the sleeve assembly into the cap 101 is equivalent to the fitting of the sleeve assembly into the cartridge housing of the first embodiment.

The order in which the component parts described above are assembled is as follows. The light spring 26 is placed in a position around the inner syringe sleeve 24. The inner syringe sleeve 24 is located within the outer syringe sleeve 25. The pull off cap 101 is then pushed onto the outer syringe sleeve 25 until the annular rim 34 clips into a corresponding annular recess 122 on the inside of the cap 101. The syringe 16 is then pushed within the sleeve and cap assembly until the rubber septum 20 locates in the cylindrical protrusion 120 of the cap 101. The complete syringe, sleeve and cap assembly is then pushed within the actuating device 10 until the lugs 117 locate behind the corresponding lugs 125 on the inside of the internal shaft 41; in this position, the rim of the cap 101 locates against the bottom of the internal shaft 41.

As mentioned above, the device is delivered to the user in this ready to use state. As mentioned in relation to FIG. 12, the first step in using the administering device is to remove the pen clip 102. Next, the pull off cap 101 is removed. The removal of the cap is now described in detail. As the cap is pulled a distance X to the position shown in FIG. 15, it will tend to pull the syringe 16, and thus the inner syringe sleeve 24, with it. This is because the rubber septum 20 which surrounds the syringe needle is at this stage held within the cylindrical protrusion 120 of the pull off cap 101. However, after this distance X has been travelled, as described above in relation to the first embodiment, the syringe 16 can move no further and therefore a further pull on the cap 101 will remove the cap from the administering device, this pull will also disengages the rubber septum 20 from the syringe barrel 17. The separation of the cap and the septum is seen in FIG. 16. Although in FIG. 15 it appears that the syringe needle 19 extends out of the syringe sleeve 107, as soon as the rubber septum 20 disengages from the syringe barrel 17, the force of the spring 26 between the inner and outer syringe sleeves 24, 25 will move the syringe 16 back into the device. Thus, the needle 19 is still safely shielded from the user.

Now that the syringe 16 has returned to its position as shown in FIG. 14, the administering device 10 is essentially in the same state as illustrated in FIG. 7. The operation of the administering device is therefore as described in relation to FIGS. 7 to 10. Very briefly, the device is pressed by the user against a relevant injection area so that the outer sleeve 25 and the inner shaft 41 move inwardly relative to the outer casing 40. Next, the actuating button 66 is depressed. These two movements allow the release of the pusher arm 46 which is then urged by the main spring 48 to move the syringe 16 forward and then depress the plunger 18 to inject the pharmaceutical substance into the user.

Immediately after use, the pull off cap 101 may be pushed back onto the device 10, thus covering the exposed needle 19, and the entire assembly can then be safely disposed of.

The third embodiment disclosed in FIGS. 17 to 24 is similar to the first embodiment in that the user sets the pusher arm 46 and cocks the main spring 48 of the actuating device, and loads the syringe assembly. The principal difference in this embodiment is that it is the loading of the syringe assembly which moves the pusher rod 46 within the actuating device and therefore the syringe is loaded into the administering device and the main spring 48 is cocked in a single action. After the syringe 16 is loaded and the spring 48 is cocked, the device is actuated in essentially the same manner as the earlier embodiments. In other words, the syringe 16 is only released following the movement of the internal shaft 41 relative to the external casing 40 and following the depression of the actuating button 66.

There are substantial similarities between this embodiment and the first embodiment and therefore where appropriate the same reference numerals are used and description is not repeated.

Figure 17:
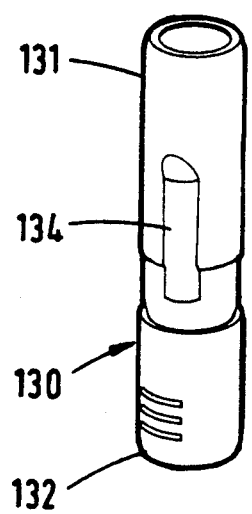
FIG. 17 is a perspective view of a syringe cartridge for use in the third aspect of the invention.
Figure 18:
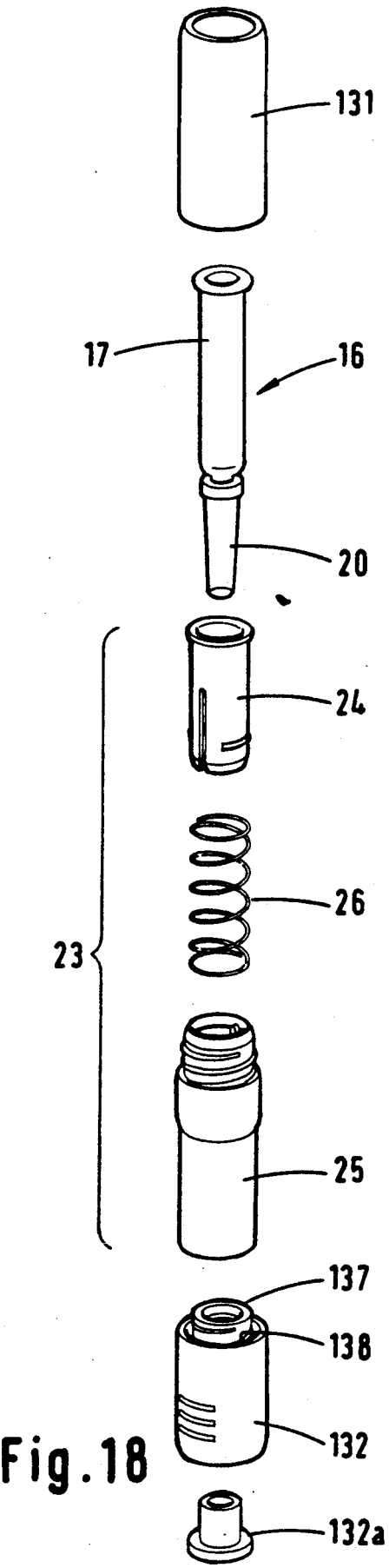
FIG. 18 is an exploded perspective view of the cartridge of FIG. 17, FIGS. 19 to 21 are sectional views of an administering device according to the third aspect of the invention, showing the loading of the syringe.

In this embodiment, it is intended that the user has an actuating device 10 and a supply of syringes 16. The syringe assemblies are disposable, but the actuating device is retained by the user for future use. A complete syringe cartridge 130 is illustrated in FIGS. 17 and 18. The cartridge comprises a first cap 131 and a second cap 132, both caps being fitted onto the syringe sleeve assembly 23. A tamper evident seal 134 is provided which covers a part of the first cap 131 and a part of the sleeve assembly 23 so that the user can be sure that the syringe 16 is intact and has not been touched previously. The first cap 131 is removed when the syringe 16 is to be mounted on the actuating device 10. After the syringe 16 is so mounted, the second cap 132 becomes the main cap of the entire administering device, as in the second embodiment.

As shown in the exploded view of FIG. 18, the syringe cartridge comprises the syringe 16, including the barrel 17 and the rubber septum 20, a light spring 26, together with the syringe sleeves 24 and 25 the first and the second cap 131, 132 as previously described. The second cap 132 includes an end cap 132a which is fixedly mounted therein. The second cap 132 has an internal hollow cylindrical protrusion 137 which has an external screw thread 138, the second cap 132 thus being able to be screwed onto the outer syringe sleeve 25, the outer sleeve having a corresponding thread on its inner surface. The cylindrical protrusion 137 is equivalent to the protrusion 37 in the first embodiment and the protrusion 120 in the second embodiment.

It will be appreciated that the syringe sleeve assembly 23 is, apart from the internal thread on the outer sleeve 25, identical to the sleeve assembly 23 of the first embodiment which is shown in FIG. 3.

With the second cap 132 screwed onto the outer sleeve 25, the syringe 16 is push fitted into the sleeve assembly as previously described in relation to the earlier embodiments.

It should be noted that when the syringe 16 is mounted within the sleeve assembly 23, the lower end of the syringe barrel 17 rests against the rim of the cylindrical protrusion 137. Movement of the syringe barrel 17 further into the sleeve assembly 23 is thus prevented.

Figures 19, 20, 21:
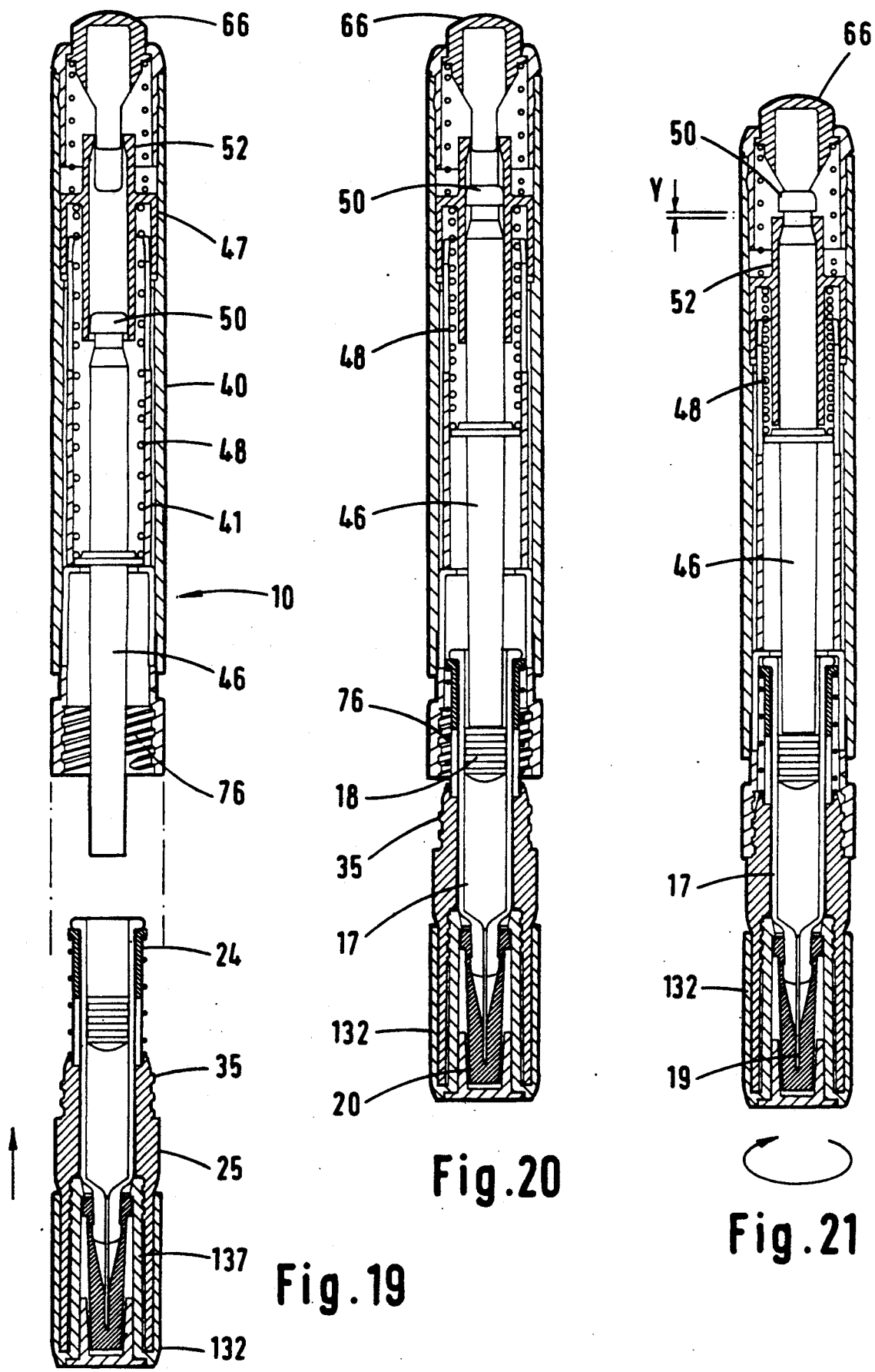

The assembled syringe, sleeves and cap is shown clearly in the lower part of FIG. 19. In this figure, the first cap 131 has already been removed. As indicated by the arrow, the syringe, sleeve and cap assembly is next pushed into the actuating device 10 in order to load the syringe 16 and simultaneously cock the main spring 48 of the actuating device.

The inner syringe sleeve 24 slides within the internal shaft 41 of the actuating device 10. The pusher arm 46 locates within the syringe barrel 17 until it reaches the rubber stopper 18 of the syringe. Further movement of the syringe and sleeve assembly into the actuating device 10 forces the pusher arm upwards 46, as seen in FIG. 20. The syringe 66 is prevented from moving downwards because of the contact between the lower end of the syringe barrel 17 and the rim of the cylindrical protrusion 137 of the cap 132. The stopper 18 cannot move downwards because the tip of the syringe needle 19 is sealed in the rubber septum 20 and thus the contents of the syringe cannot be expelled.

In this way, the syringe and sleeve assembly is pushed into the actuating device 10 until the head 50 of the pusher arm 46 approaches the arms 52 of the retention slip 47. The syringe and sleeve assembly is then rotated so that the screw thread 35 of the outer syringe sleeve 25 engages with the corresponding screw thread 76 on the inner surface of the internal shaft 41. The screwing of the outer sleeve 25 into the internal shaft 41 pushes the head 50 of the pusher arm 46 over the arms 52 to cock the main spring 48.

The movement of the syringe and sleeve assembly into the actuating device is illustrated in FIG. 20 and 21. As illustrated in FIG. 21, when the screw thread 35 of the syringe sleeve 25 and the screw thread 76 of the internal shaft are engaged, the pusher arm 46 is held in a position wherein the head 50 is a small distance Y above the arms 52 of the retention slip 47. This distance Y is present to allow for manufacturing tolerances in the different parts making up the entire assembly. The presence of this additional distance Y in the device does not affect its operation, as will become apparent.

It may be mentioned that, in this embodiment, there is no need for the pen clip 102 of the second embodiment, since the pusher arm 46 is prevented from moving into the device by the cap 132 being screwed onto the syringe sleeve 25 and thus the stopper 18 moving against the pusher rod 46.

It will be apparent that the presence of the cap 132 on the syringe sleeve 25 is essential to the movement of the pusher arm 46 within the actuating device 10 and thus the cocking of the main spring 48. If the cap were not present, when the sleeve assembly 23 was pushed within the internal shaft 41, the syringe 16 and/or the syringe stopper 18 would simply move downwardly. Moreover, the presence of the cap 132 acts as a reassurance to the user that there is no danger of the needle becoming exposed. This reassurance is most preferable since the syringe and sleeve assembly will be held in the hand of the user when cocking the spring.

As mentioned above, FIG. 21 shows the administering device 10 with the main spring 48 cocked. To use the device and release the syringe, the following steps are necessary as described in relation to FIGS. 22 to 24. These steps are similar to those described in relation to FIGS. 14 to 16 showing the second embodiment.

Figure 22:
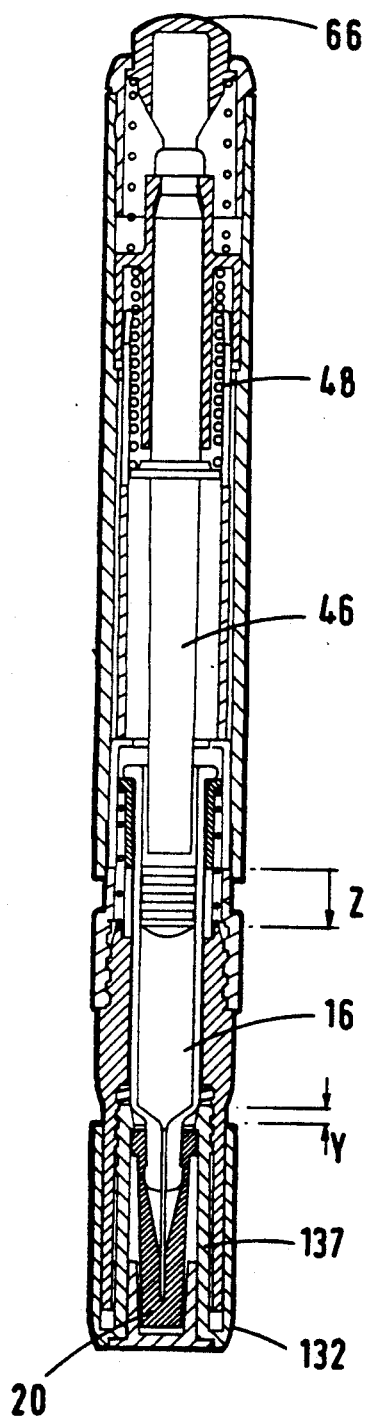
FIGS. 22 to 24 are sectional views, similar to FIGS. 19 to 21, showing the steps for preparing the device for use.

Firstly, as indicated by the circular arrow in FIG. 22, the cap 132 is unscrewed. The initial downward movement of the cap by the distance Y allows the syringe 16 to be moved within the syringe sleeve assembly 23 and thus allows the pusher arm 46 to move forward to a position where the head 50 of the pusher arm 46 contacts the retention clip 47.

Further unscrewing of the cap 132 tends to pull downward the syringe 16 within the syringe sleeve assembly 23 because the rubber septum 20 is held within the circular protrusion 137 of the cap. Thus, the syringe 16 tends to move downward a further distance Z.

Figure 23:
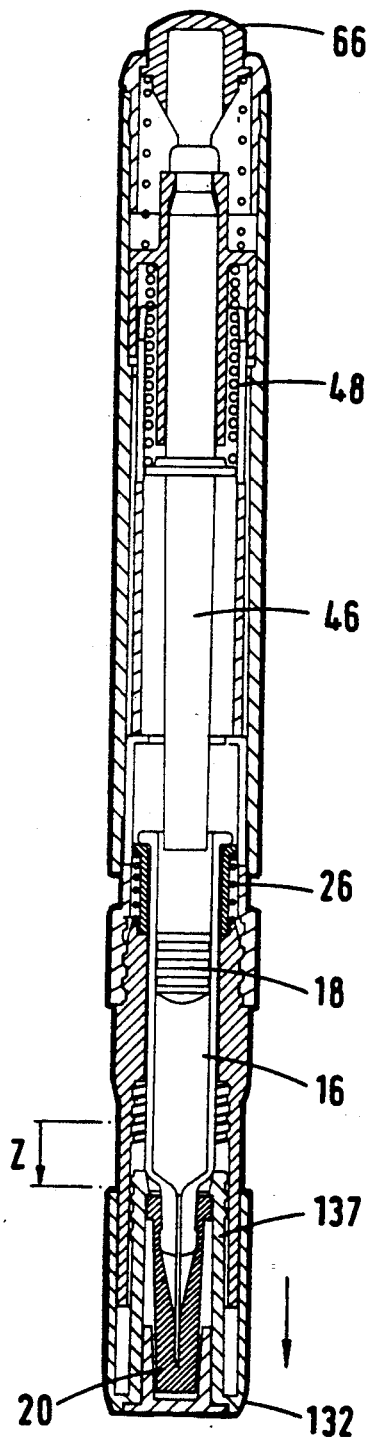

However, when the cap 132 comes to the position shown in FIG. 23, further movement of the syringe 16 is prevented by the cooperation of the webs 29 and slots 28, as previously described. In this position, the threads of the cap 132 and the syringe sleeve 25 are already disengaged and the cap 132 can be pulled off. The pulling off of the cap 132 also disengages the rubber septum 20 from the syringe, thus exposing the needle 19.

When the cap is removed, the spring 26 of the syringe sleeve assembly 23 immediately moves the syringe back to the position shown in FIG. 22 so that the needle 19 is not exposed.

Figure 24:
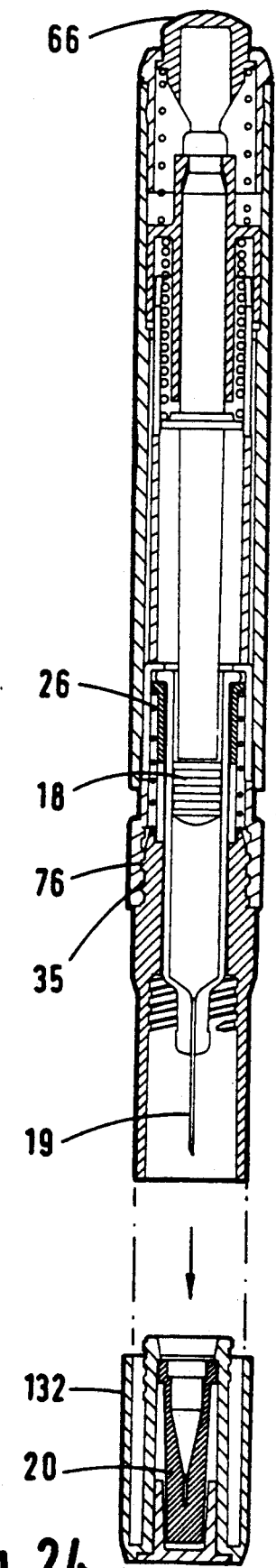

This position is shown in FIG. 24 and the administering device 10 is now ready for use. The actuation of the device is as described in relation to the previous embodiments and so is not described again here.

After use, the needle 19 is in an exposed condition but can be safely protected by remounting the cap 132 onto the syringe sleeve. The syringe sleeve assembly 23 complete with the cap 132, can then be released from the actuating device 10 by disengaging the screw threads 35 and 76. The first cap 131 is next remounted on the syringe sleeve assembly. This assembly of the syringe, sleeves and cap can therefore be disposed of and the actuating device is now ready for a further syringe to be mounted therein.

What we claim is:

1. An administering device comprising:
    a body for holding a container of substance to be administered, a release mechanism, means controlled by the release mechanism to discharge the said substance, and a trigger, the release mechanism being capable of releasing the discharge means by cooperating with the trigger;
    wherein the body is formed of two parts, a first part and a second part, the two parts being movable relative to one another along a predetermined axis between a first and a second position;
    wherein the trigger is mounted on the first part and the release mechanism is is mounted on the second part; whereby the trigger is movable substantially along said predetermined axis between the first position and the second position in a direction towards the release mechanism;
    wherein, in the second position, the release mechanism is nearer to the trigger than in the first position; and
    wherein only in the second position is the trigger capable of cooperating with the release mechanism to release the discharge means, whereby the discharge means cannot be accidentally released.

2. An administering device according to claim 1, wherein said second part is slidably mounted within said first part and extends out of said first part.

3. An administering device according to claim 2, wherein the release mechanism is mounted at an end of the second part, the trigger of the first part being in the form of a push button towards which the release mechanism is moved by movement of the second part with the first part.

4. An administering device according to claim 3, wherein the container is a syringe held within the said second part and wherein actuation of the discharge means firstly moves the syringe forward within the second part to expose the needle, and thus to urge it through the skin, and secondly depresses the plunger of the syringe to administer the substance to the user.

5. An administering device according to claim 4, wherein the discharge means is an elongate pusher rod which is urged by means of a resilient force and wherein the release mechanism comprises a pair of arms over which the end of the pusher rod is held, the rod being released by relative movement of the button to separate the arms.

6. An administering device according to claim 5, wherein the one part of the device which moves within the other is itself comprised of two parts, a first part extending out of the device and being in the form of a sleeve which houses the syringe and a second part within the device which houses the pusher rod, the first and second parts of the one part being releasably connectable together.

7. An administering device according to claim 6, wherein the said sleeve comprises an inner and an outer sleeve part, the sleeve parts being movable relative to each other against the action of a spring.

8. An administering device according to claim 1, wherein the administering device is elongate and generally cylindrical and thus is similar to a pen in shape.

9. An administering device according to claim 1, wherein the said substance is a pharmaceutical substance useful in treating migraine and related disorders such as cluster headache.

10. An administering device according to claim 9, wherein the pharmaceutical substance is sumatriptan.

11. A combination of an administering device according to claim 1 and a housing for at least one container of the substance to be discharged, the housing comprising a removable sleeve for the container and means releasably holding the sleeve within the housing, the said sleeve having means to releasably attach itself to the first part of the administering device, whereby the sleeve and container can be removed from the housing by co-operation with the administering device and can be returned to the housing after use.

12. A combination according to claim 11, wherein the housing has a lid which is closed after the used container is returned thereto.

13. A combination according to claim 11, wherein the container is a syringe having a rubber cap protecting the needle, this cap remaining within the housing when the sleeve is removed by the administering device.

14. A combination according to claim 13, wherein the syringe is held within the sleeve against the action of a spring.

15. A combination according to claim 11, together with a casing for the combination, the casing having a recess for the administering device, the recess including means to prime the release mechanism when the device is placed into the recess.

16. An administering device according to claim 1, wherein the container is moveable within the body against the discharge means and wherein the device further comprises means to prevent discharge of the substance until the discharge means is engaged by the release mechanism, whereby the loading of the container into the body can simultaneously engage the discharge means with the release mechanism.

17. An administering device according to claim 16, wherein the container is a syringe and a rubber cap is provided over the syringe needle to seal the syringe so that the syringe itself can be used to move the discharge means.

* * * * *